(12) United States Patent
Hanaki et al.

(10) Patent No.: US 7,341,346 B2
(45) Date of Patent: Mar. 11, 2008

(54) OCULAR ACCOMMODATIVE FUNCTION EXAMINATION APPARATUS

(75) Inventors: Miwako Hanaki, Gamagori (JP); Noriji Kawai, Gamagori (JP); Naoki Isogai, Nishio (JP)

(73) Assignee: Nidek Co., Ltd., Aichi-ken (JP)

( * ) Notice: Subject to any disclaimer, the term of this patent is extended or adjusted under 35 U.S.C. 154(b) by 7 days.

(21) Appl. No.: 11/013,358

(22) Filed: Dec. 17, 2004

(65) Prior Publication Data
US 2005/0146685 A1 Jul. 7, 2005

(30) Foreign Application Priority Data
Dec. 22, 2003 (JP) ............................. 2003-425948

(51) Int. Cl.
*A61B 3/10* (2006.01)
(52) U.S. Cl. ....................................... 351/205; 351/211
(58) Field of Classification Search ........ 351/108–211, 351/221
See application file for complete search history.

(56) References Cited

U.S. PATENT DOCUMENTS

| | | | |
|---|---|---|---|
| 5,463,430 | A | 10/1995 | Isogai et al. |
| 6,361,168 | B1 * | 3/2002 | Fujieda ........................ 351/208 |
| 6,439,720 | B1 * | 8/2002 | Graves et al. ............... 351/211 |
| 6,511,180 | B2 * | 1/2003 | Guirao et al. ............... 351/211 |
| 6,535,757 | B2 * | 3/2003 | Ono ............................. 600/476 |
| 2005/0007551 | A1 * | 1/2005 | Wakil et al. ................ 351/205 |

FOREIGN PATENT DOCUMENTS

JP A 2003-070740 3/2003

OTHER PUBLICATIONS

Setsuko Suzuki et al.; "Evaluation of Accommodative Function by High Frequency Component of Accommodative Microfluctuation"; pp. 93-97; Visual Science, vol. 22 No. 3; Sep. 2001.

* cited by examiner

Primary Examiner—Huy K Mai
(74) Attorney, Agent, or Firm—Oliff & Berridge, PLC

(57) ABSTRACT

An ocular accommodative function examination apparatus for examining an accommodative function of an examinee's eye, comprises: a fixation target presenting optical system which presents a fixation target at a presenting position to the eye, the presenting position being changeable in a direction of a visual axis of the eye; a refractive power measuring optical system which measures refractive power of the eye and includes a light projecting optical system which includes a light source and projects examination light to a fundus of the eye and a light receiving optical system which includes a light receiving element and receives the examination light reflected from the fundus; an analysis part which acquires variation or fluctuation in the refractive power in a specified measurement meridian direction of the eye gazing at the fixation target at a certain presenting position within a predetermined time based on output of the light receiving element, and determines the accommodative function of the eye based on the acquired variation or fluctuation; an output part which outputs a result determined by the analysis part; and a correcting device which corrects the refractive power determined in the specified measurement meridian direction based on astigmatic power and an astigmatic axis angle when the eye has astigmatism; wherein the analysis part determines the accommodative function based on the corrected refractive power.

5 Claims, 6 Drawing Sheets

OCULAR ACCOMMODATIVE FUNCTION EXAMINATION APPARATUS

BACKGROUND OF THE INVENTION

1. Field of the Invention

The present invention relates to an ocular accommodative function examination apparatus for examining an accommodative function of an examinee's eye.

2. Description of Related Art

When refractive power of an eye of an examinee who gazes at a target (optotype) is objectively observed (detected) with time, the refractive power exhibits fluctuation like a sine wave, called accommodative microfluctuation. This accommodative microfluctuation is separated into a high frequency component (1.0-2.3 Hz) and a low frequency component (less than 0.6 Hz). In recent years, attention has been given to that the "frequency of occurrence (spectral power) of the high frequency component" (hereinafter, HFC) of the accommodative microfluctuation has certain correlation with the degree of accommodative constriction (excessive tonic accommodation, accommodative spasm); e.g., the HFC increases as a burden (constriction) on the ciliary muscle becomes larger. Based on this point of view, there has been proposed a method for examining the degree of the accommodative constriction by examining the HFC (see "Evaluation of accommodative function by HFC of accommodative microfluctuation", Visual Science, Vol. 22 No. 3) Because it is thought that accommodation abnormal is one of causes of asthenopia (eyestrain, eye fatigue), knowing the degree of the accommodative constriction is meaningful.

SUMMARY OF THE INVENTION

The present invention has been made in view of the above circumstances and has an object to provide an ocular accommodative function examination apparatus capable of efficiently and precisely examining an accommodative function of an eye.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided an ocular accommodative function examination apparatus for examining an accommodative function of an examinee's eye, comprising: a fixation target presenting optical system which presents a fixation target at a presenting position to the eye, the presenting position being changeable in a direction of a visual axis of the eye; a refractive power measuring optical system which measures refractive power of the eye and includes a light projecting optical system which includes a light source and projects examination light to a fundus of the eye and a light receiving optical system which includes a light receiving element and receives the examination light reflected from the fundus; an analysis part which acquires variation or fluctuation in the refractive power in a specified measurement meridian direction of the eye gazing at the fixation target at a certain presenting position within a predetermined time based on output of the light receiving element, and determines the accommodative function of the eye based on the acquired variation or fluctuation; an output part which outputs a result determined by the analysis part; and a correcting device which corrects the refractive power determined in the specified measurement meridian direction based on astigmatic power and an astigmatic axis angle when the eye has astigmatism; wherein the analysis part determines the accommodative function based on the corrected refractive power.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

Figure 1:
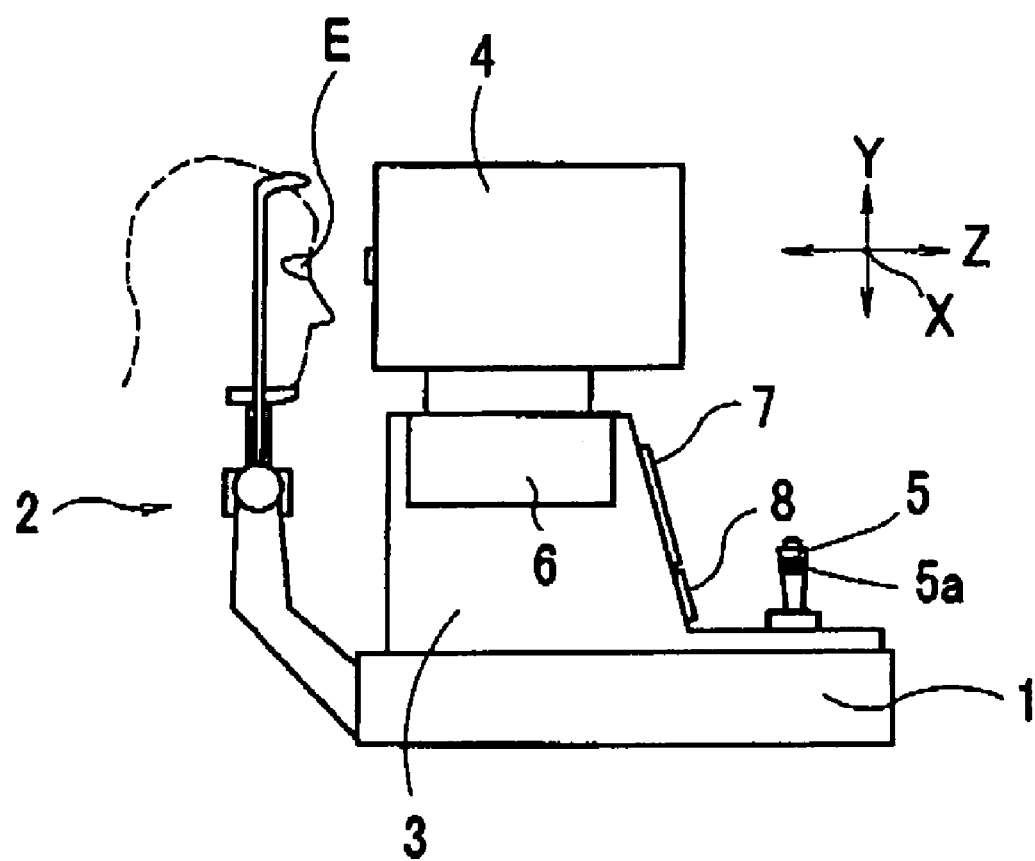
FIG. 1 is a schematic external view of an ocular accommodative function examination apparatus.

A detailed description of a preferred embodiment of an ocular accommodative function examination apparatus embodying the present invention will now be given referring to the accompanying drawings. FIG. 1 is a schematic external view of the ocular accommodative function examination apparatus in the present embodiment. The examination apparatus includes a base 1, a head support unit 2 fixed to the base 1, a movement carriage 3 which is movably placed on the base 1, and a measurement (examination) part 4 which is movably placed on the movement carriage 3 and houses optical systems which will be mentioned later. The measurement part 4 is moved in a rightward/leftward direction (X-direction), an upward/downward direction (Y-direction), and a backward/frontward direction (Z-direction) with respect to an eye E of an examinee by a moving part 6 provided in the movement carriage 3. The moving part 6 is constructed of a sliding mechanism and a motor provided for each of the X-, Y-, and Z-directions, and others. The movement carriage 3 is moved on the base 1 in the X- and Z-directions respectively by tilting operation of a joystick 5. Further, the measurement part 4 is moved in the Y-direction by rotating operation of a rotary knob 5a. The movement carriage 3 is provided with a monitor 7 which displays an image of the eye E for observation and various information such as examination results, a switch part 8 on which many switches are arranged, and others.

Figure 2:
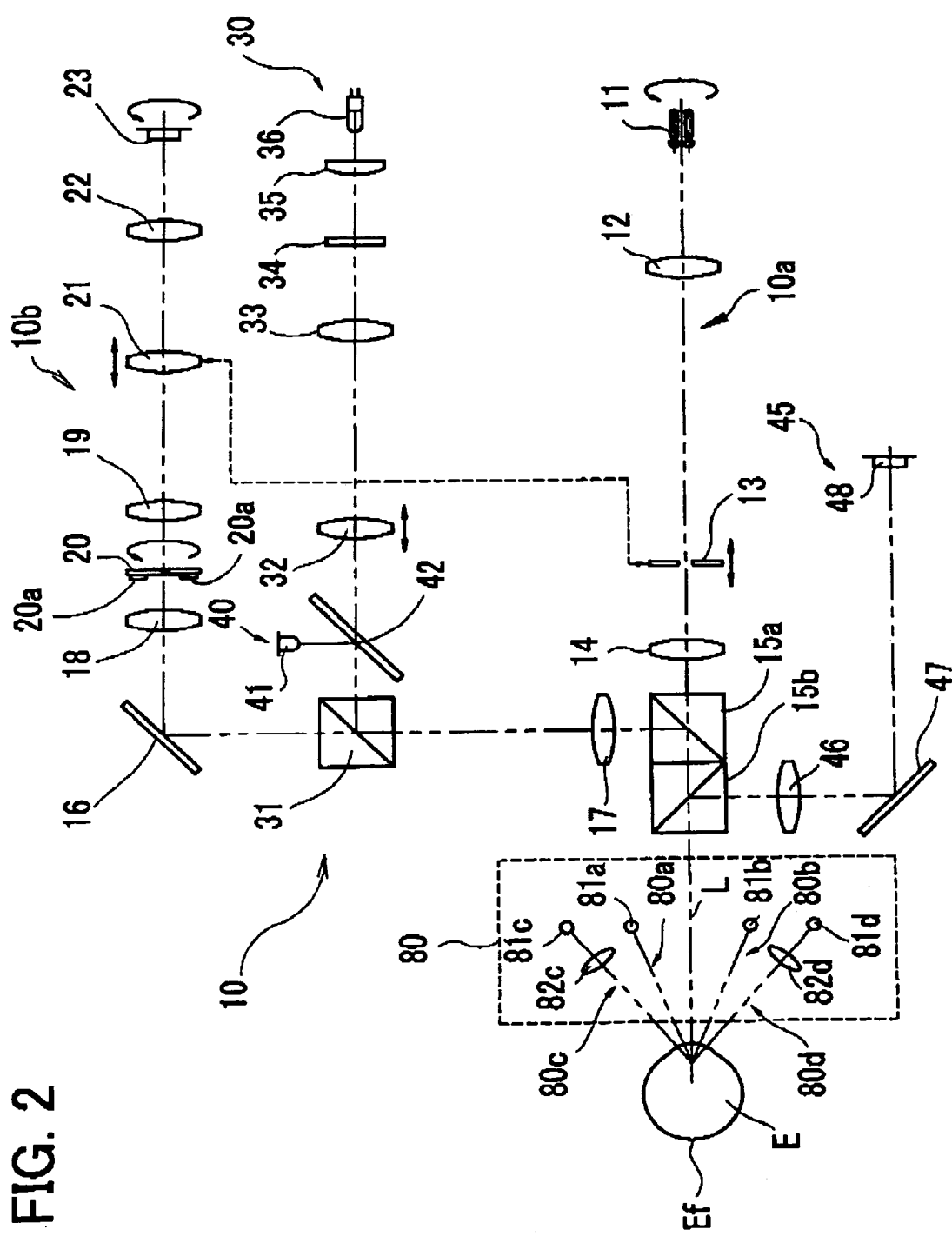
FIG. 2 is a schematic structural diagram of an optical system of the examination apparatus.

FIG. 2 is a schematic structural diagram of optical systems of the examination apparatus, including an eye refractive power measuring optical system 10, a fixation target presenting optical system 30, a first alignment target projecting optical system 40, a second alignment target projecting optical system 80, and an observation optical system 45, which will be mentioned below in detail.

The eye refractive power measuring optical system 10 includes a light projecting optical system 10a and a light receiving optical system 10b. Infrared examination (measurement) light emitted from two examination (measurement) light sources 11 is projected to a fundus Ef of the eye E through a condensing lens 12, an examination (measurement) target plate 13, a projection lens 14, and half mirrors 15a and 15b in order. The examination light reflected from the fundus Ef is received by a light receiving element (photodetector) 23 for examination (measurement) through the half mirror 15b, the half mirror 15a, an objective lens 17, a half mirror 31, a reflection mirror 16, a relay lens 18, a strip-shaped mask 20 for blocking corneal reflection light, a relay lens 19, a movable lens 21, and an image forming lens 22 in order. The light sources 11, the mask 20, and the light receiving element 23 are disposed to be synchronously rotatable about an optical axis (path) L. The target plate 13 has a target (a spot opening) for examination (measurement) and is disposed to be moved along the optical axis L to an optically and substantially conjugate position with the fundus Ef. The lens 21 is disposed to be moved along the optical axis L together with the target plate 13. The mask 20 is disposed in an optically and substantially conjugate position with a cornea Ec of the eye E. Further, the mask 20 is provided with two light receiving elements (photodetectors) 20a into which the reflection light from the cornea Ec or an anterior segment of the eye E enters, that is, which receive the reflection light. Based on signals outputted from the light receiving elements 20a, the presence of blinks of the eye E, the presence of factors interfering with measurement (examination) in a measurement (examination) meridian direction, and others are detected.

In the fixation target presenting optical system 30, visible light emitted from a light source 36 passes through a condensing lens 35 and illuminates a fixation target (stimulus target) provided on a fixation target plate 34. The fixation target light is projected to the fundus Ef through relay lenses 33 and 32, a dichroic mirror 42, the half mirror 31, the lens 17, and the half mirrors 15a and 15b in order. The dichroic mirror 42 has the property of allowing visible light to pass therethrough and reflecting infrared light. The fixation target on the fixation target plate 34, which is commonly used as a fixation target, is positioned at a focal point of the lens 33. The lens 32 is disposed to be movable on the optical axis L (its moving distance (amount) is proportional to a spherical power of the examinee's eye), thereby optically changing a presenting position (distance) of the fixation target in a direction of the visual axis of the eye E. In the measurement of eye refractive power, the lens 32 is moved to apply a fogging to the eye E in order to relieve (relax) the accommodation of the eye E. In an alternative, the change of the presenting position of the fixation target may be made by moving the fixation target plate 34, lens 35, and light source 36 in combination along the optical axis L.

The first alignment target projecting optical system 40 is constructed to project a target to the cornea Ec from a direction along the visual axis of the eye E, the target being used for alignment in the X- and Y-directions. In this optical system 40, infrared alignment light (alignment target) emitted from a point light source 41 is projected to the cornea Ec from front along the optical axis L by way of the dichroic mirror 42, the half mirror 31, the lens 17, and the half mirrors 15a and 15b in order.

The second alignment target projecting optical system 80 is constructed to project a target to the cornea Ec from an oblique direction with respect to the direction of the visual axis of the eye E, the target being used for alignment in the Z-direction. This optical system 80 includes two first target projecting optical systems 80a and 80b disposed in symmetrical relation with respect to the optical axis L and two second target projecting optical systems 80c and 80d disposed outside the first target projecting optical systems 80a and 80b (farther away than the optical system 80a and 80b from the optical axis L) in symmetrical relation with respect to the optical axis L. Infrared alignment light (alignment targets) emitted from point light sources 81a and 81b of the first target projecting optical systems 80a and 80b is projected to the cornea Ec (the alignment targets are projected at finity). Infrared alignment light (alignment targets) emitted from point light sources 81c and 81d of the second target projecting optical systems 80c and 80d is projected to the cornea Ec through collimating lenses 82c and 82d (the alignment targets are projected at infinity). The first target projecting optical systems 80a and 80b are disposed so that their projecting optical axes intersect with the optical axis L at a first predetermined angle. The second target projecting optical systems 80c and 80d are disposed so that their projecting optical axes intersect with the optical axis L at a second predetermined angle larger than the first predetermined angle.

In the observation optical system 45, an image of the anterior segment of the eye E illuminated by infrared light emitted from an illumination light source not shown and an image of each of the alignment targets projected by the target projecting optical systems 40 and 80 are photographed (picked up) by a CCD camera 48 through the half mirror 15b, an objective lens 46, and a reflection mirror 47 in order.

Figure 3:
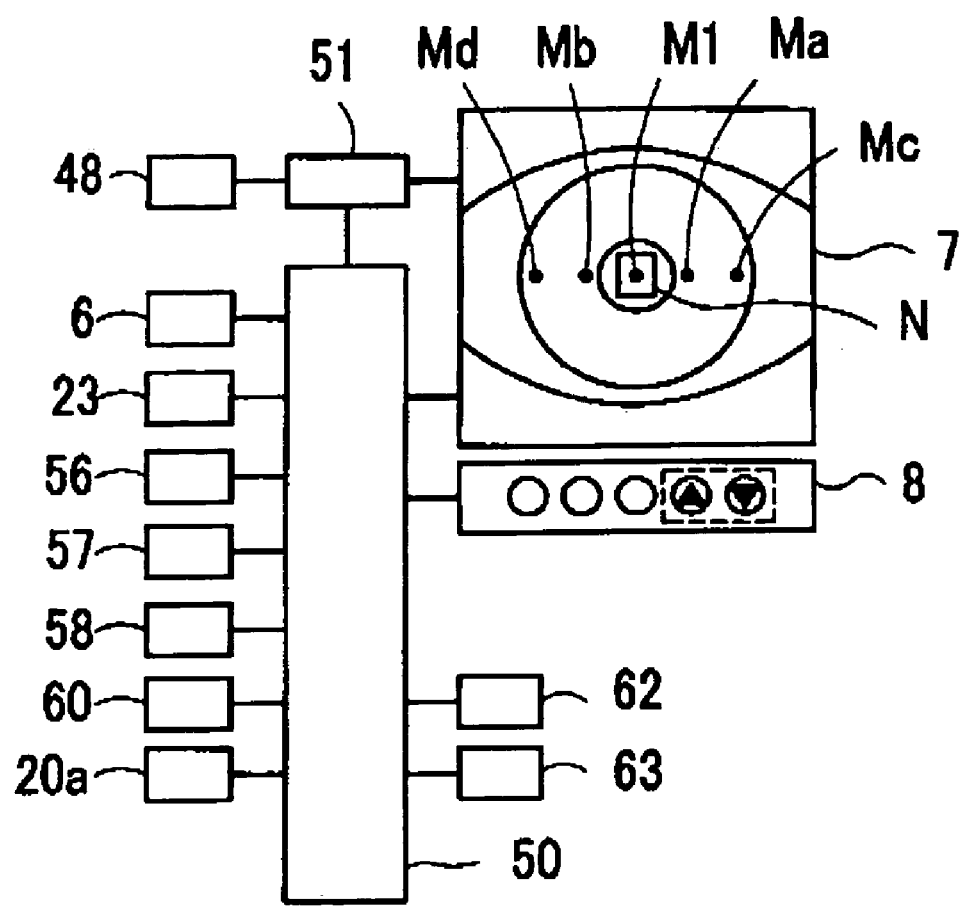
FIG. 3 is a schematic structural diagram of a control system of the examination apparatus.

FIG. 3 is a schematic structural diagram of a control system of the examination apparatus. An image signal from the camera 48 is inputted to an image processing part 51 and is outputted to (displayed on) the monitor 7. To an analysis and control part 50, connected are the moving part 6, the monitor 7, the image processing part 51, the switch part 8, the light receiving element 23, a motor 56 for rotating the light sources 11, the mask 20 and the light receiving element 23, a motor 57 for moving the target plate 13 and the lens 21, a potentiometer 60 for detecting a moved position (movement distance) of the target plate 13 (or the lens 21), a motor 58 for moving the lens 32, the light receiving element 20a, a memory 62, a sound generator 63, and others. The analysis and control part 50 controls the above components and also determines eye refractive power based on output signals of the light receiving element 23 and the potentiometer 60 and further determines an accommodative function.

The examination of an accommodative function (accommodative constriction) using the apparatus constructed as above is explained below with reference to FIG. 4. An examiner requests an examinee to rest his head on the head support unit 2 and makes alignment of the measuring optical system 10 (the optical axis L) with respect to the eye E. This embodiment exemplifies the case where an automatic alignment mode and an automatic tracking mode are selected.

Firstly, a regular measurement for distance refractive power is executed (S1). While observing an image of the anterior segment of the eye E and a reticle N both displayed on the monitor 7, the examiner operates the joystick 5 and the rotary knob 5a to move the movement carriage 3 and the measurement part 4 in the X-, Y-, and Z-directions for rough alignment. As shown in FIG. 3, when an alignment target image M1 generated by means of the target projecting optical system 40 and four alignment target images Ma to Md generated by means of the target projecting optical system 80 appear on the monitor 7, the automatic alignment and the automatic tracking are performed. The target image M1 and the target images Ma to Md are photographed by the camera 48 and are detected and processed in the image processing part 51. The analysis and control part 50 determines whether an alignment state in the X- and Y-directions is proper based on a result of the detection of the centered target image M1. Further, the analysis and control part 50 determines whether an alignment state in the Z-direction is proper based on results of the detection of the target images Ma to Md.

The determination of the alignment state in the Z-direction is executed by a comparison between an image distance (image height) of the infinite target images Mc and Md generated by the second target projecting optical systems 80c and 80d and an image distance (image height) of the finite target images Ma and Mb generated by the first target projecting optical systems 80a and 80b. In the case of projection of a target at infinite, an image distance (image height) of the target image substantially remains unchanged even when a working distance (a distance in the Z-direction) is changed. In the case of projection of a target at finite, on the other hand, an image distance (image height) of the target image changes according to changes in working distance. This characteristics may be utilized to determine an alignment state in the Z-direction (see U.S. Pat. No. 5,463,430 corresponding to Japanese unexamined patent publication No. H6(1994)-46999).

The analysis and control part 50 drivingly controls the moving part 6 based on results of the determination of the alignment states in the X-, Y-, and Z-directions to move the measurement part 4 in respective directions. When all of the alignment states in the above directions fall within a predetermined allowable range (proper range), the analysis and control part 50 automatically generates a trigger signal to start measurement.

The examination light from the light sources 11 is converged to a point near the cornea Ec and reaches the fundus Ef. If the eye E is normal, an image of the examination target (light) reflected by the fundus Ef is formed on the light receiving element 23. If the eye E has abnormal refractive power (refractive error), the analysis and control part 50 drives the motor 57 based on an output signal from the light receiving element 23 to move the target plate 13 and the lens 21 to the optically and substantially conjugate position with the fundus Ef.

Next, the analysis and control part 50 drives the motor 58 to move the lens 32, thereby bringing the fixation target plate 34 to an optically and substantially conjugate position with the fundus Ef, and thereafter move the lens 32 again so that a fogging is applied by an appropriate diopter to relieve (relax) the accommodation of the eye E. In this state where the eye E is fogged, the analysis and control part 50 drives the motor 56 to rotate the light sources 11, the mask 20 and the light receiving element 23, 180° about the optical axis L. During the rotation, the analysis and control part 50 drives the motor 57 based on an output signal from the light receiving element 23 to move the target plate 13 and the lens 21. Based on results of the detection of a distance (amount) of movement of the target plate 13 or the lens 21 by the potentiometer 60, the analysis and control part 50 determines refractive power in each meridian direction. The analysis and control part 50 applies predetermined processing to this refractive power to determine each of refractive power values S(spherical power), C(cylindrical power), and A(astigmatic axis angle). The determined refractive power values S, C, and A in a nonaccommodative state (fogged state) are stored in the memory 62.

After the distance refractive power measurement, continuously, the examination of a accommodative function is conducted (S2 to S6). On the basis of the position of an S value (which can be regarded as a far point of the eye E) of distance refractive power in the aforementioned nonaccommodative state, a presenting position of a fixation target is changed (moved) to a far position by +0.5 D. Variation (fluctuation) in refractive power within a predetermined time T (e.g., 20 seconds) at this presenting position is acquired.

It is to be noted that the time T during which the variation in refractive power is acquired is not limited to 20 seconds mentioned above and it may be changed according to the amount of data needed for a calculation of the HFC. For instance, if a target for the calculation of the high frequency component of accommodative microfluctuation is set at 0.5 Hz or more, the time T is set at about 10 seconds. During this time T, data of five periods or more can be acquired, which is sufficient for the calculation of the HFC.

The period time during which variation in refractive power is acquired may be set appropriately. For example, relative to a high frequency component of up to 2.3 Hz, the variations in refractive power is acquired at period time of about 80 msec. If a higher frequency component is targeted, it is preferable to acquire variations in refractive power at shorter period time.

The measurement meridian direction in which the light source 11, mask 20, and light receiving elements 23 are positioned is set at a specified direction, so that variation in refractive power can be acquired in as short period time as 0.1 second or less. It is advantageous that this measurement meridian direction is normally set at the horizontal meridian direction of an eye. This is because, if the measurement meridian direction is the meridian direction of 90° with respect to the horizontal meridian direction, eyelid or eyelash may have an influence on measurement, leading to measurement errors or measurement deviations.

Thereafter, the presenting position of the fixation target is optically changed (moved) in steps of 0.5 D in turn to eight positions toward a near target; +0.5 D, 0.0 D, −0.5 D, −1.0 D, −1.5 D, −2.0 D, −2.5 D, and −3.0 D. Variations in refractive power within the time T at each presenting position is acquired. The acquired variations in refractive power are stored in the memory 62 in one-to-one correspondence with the presenting positions.

In the previous distance refractive power measurement in each meridian direction, if a measurement inhibition factor such as cataract is detected in the measurement meridian direction in the accommodative function examination (S3), the measurement meridian direction is changed to an appropriate direction to avoid the measurement inhibition factor (S6). The presence/absence of the measurement inhibition factor in the measurement meridian direction is detected based on the output from the light receiving element 20a on the mask 20. If the measurement inhibition factor is present, the examination light from the light sources 11 is reflected by that inhibition factor and therefore an output level of the light receiving element 20a increases. In other words, when the output level of the light receiving element 20a is higher than a reference level, it is determined that the inhibition factor is present. The measurement meridian direction is changed and set by the analysis and control part 50 based on a light received result (amount) by the light receiving element 20a in the distance refractive power measurement. Alternatively, this changing and setting operation may be performed arbitrarily by the examiner by using the switch part 8.

When the variation in the refractive power acquired at each presenting position (8 positions) is stored in the memory 62, the analysis and control part 50 executes analysis of an accommodative function (S7). Prior to this analysis, the analysis and control part 50 corrects the refractive power determined in the measurement meridian direction to refractive power in a minor meridian direction by the following equation when the result of the previously executed distance refractive power measurement exhibits that the eye E has astigmatism. In the equation, "$D_{COR}$" is corrected refractive power, "$S_H$" is refractive power (spherical power) determined in the measurement meridian direction, and "$C_{HOME}$" and "$A_{HOME}$" are cylindrical power (astigmatic power) and astigmatic axis angle respectively.

$$D_{COR}=S_H+C_{HOME}*\sin^2(A_{HOME})$$

This correction of refractive power in view of astigmatism (hereinafter, astigmatism correction) enables precise analysis and evaluation of an accommodative function in consideration of the astigmatism, even though the refractive power is measured in a specified meridian direction. For instance, when the astigmatic axis angle is 90°, which is deviated from the measurement meridian direction (wherein astigmatic power is assumed to be minus), fixation target can be seen more clearly in the vertical meridian direction because presenting of the fixation target begins with a distant target in the examination. In the case where the measurement meridian direction is the horizontal meridian direction (=0°), the refractive power determined is stronger by astigmatism. Specifically, in the case of the eye whose astigmatic power "C" is −2 D, the refractive power in the horizontal meridian direction will be determined as a larger value by −2 D. If this refractive power is directly used in the analysis and evaluation of an accommodative function, it appears as if having accommodative lead (excessive accommodation). Thus, the accommodative function cannot be analyzed and evaluated exactly. On the other hand, if the refractive power in the measurement meridian direction is corrected to the refractive power in the minor meridian direction by using the above calculation, exact analysis and evaluation of an accommodative function can be achieved.

The analysis and control part 50 calculates the HFC based on the variations in refractive power after the astigmatism correction. This calculation of HFC is briefly explained below. At first, the data checked at the time of detection of blinking of the eye E is removed from the data to be analyzed. Data loss and irregularity due to the blinking are corrected by cubic spline. Then, a frequency analysis is performed by means of a fast Fourier transform (FFT) to calculate a power spectrum (spectral power). This calculation of a power spectrum is conducted at each of intervals set within the time T (e.g. 20 seconds). Within the time T, the intervals are set to lag behind preceding ones by a predetermined time (e.g., 1 second) and have an equal duration (e.g., 8 seconds). The calculated power spectrum is converted to common logarithms and analyzed. Based on this power spectrum, a mean power spectrum (in dB) in the intervals for high frequency components of 1.0 to 2.3 Hz is determined and evaluated as the "frequency of occurrence of high frequency component" (HFC) of accommodative microfluctuation.

Figure 5:
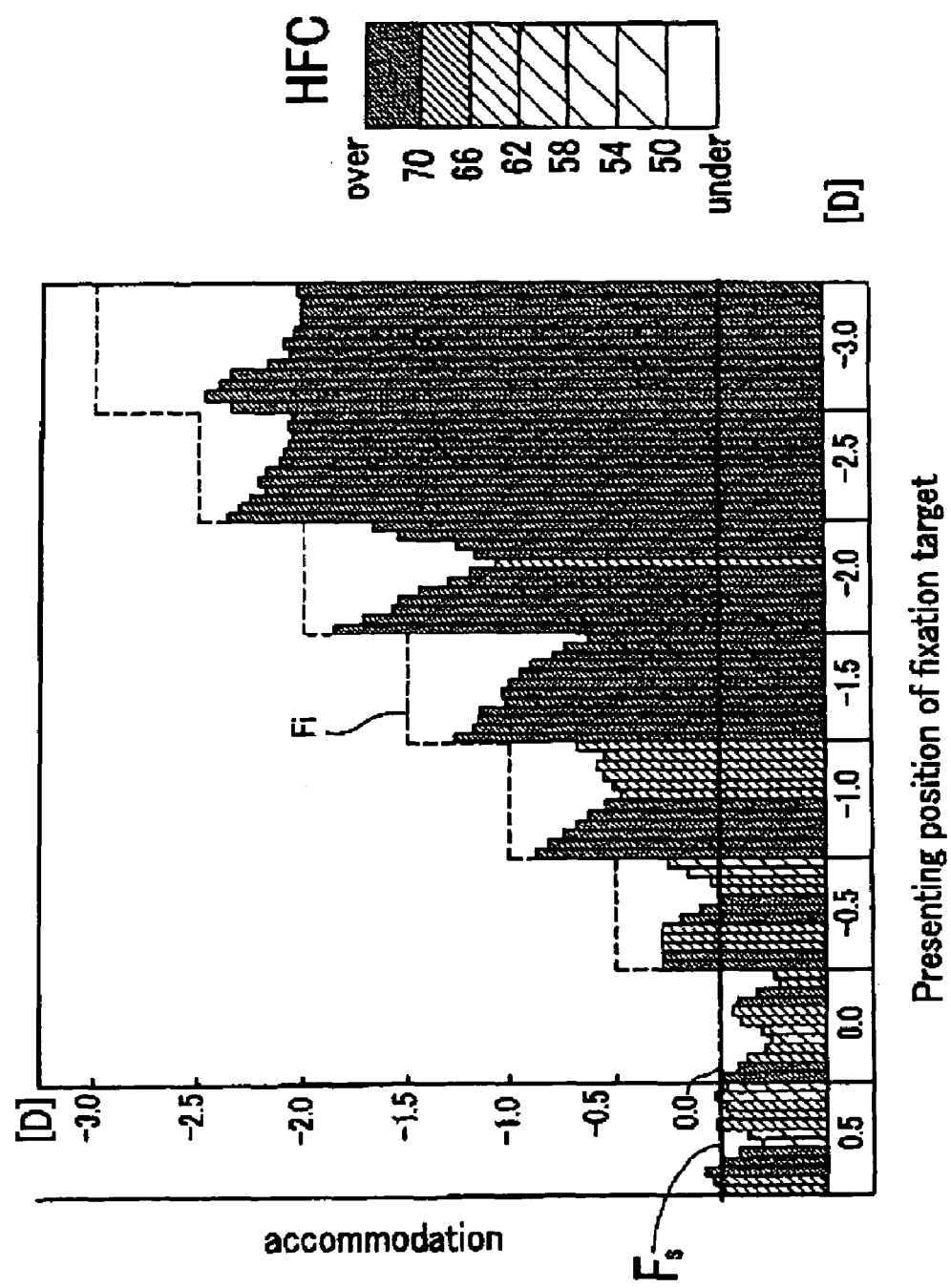
FIG. 5 is an example of a display showing results of the examination of an accommodative function.

Once the HFC is calculated, results of the examination of an accommodative function as shown in FIG. 5 is displayed on the monitor 7 (step 8). These examination results are displayed in terms of three parameters; fixation target presenting position (distance), amount of accommodation response (range of accommodation), and HFC, in the form of a three dimensional graph with color cord maps. In this graph, the vertical axis indicates the amount of accommodation response (in D) and the horizontal axis indicates the fixation target presenting position, where variation in the amount of accommodation response corresponding to elapsed times within the time T at each presenting position are graphed in a bar graph. The HFC is color-coded in for example seven levels. For example, an HFC less than 50 is displayed in green, an HFC not less than 70 is displayed in red, and other HFC therebetween is displayed with gradations in color between green through yellow to red. The HFC for a distant target is lower in the eyes with less accommodative constriction, which is expressed in green in the color cord map. The HFC is totally higher in the eyes with much accommodative constriction, which is expressed in red in the color cord map. This shows that the ciliary muscle is in a constricted state.

In FIG. 5, a single line FS indicates an S value obtained in the distance refractive power measurement and is shown in association with the amount of accommodation response at each presenting position. A dotted line Fi indicates refractive power obtained by conversion of each presenting position to refractive power (value). Herein, the analysis and control part 50 determines the followings about this analysis result (S9). If the accommodation response amount follows each presenting position (the accommodation response amount varies stepwise) but there is a large difference in accommodation response amount at the refractive power at each presenting position (for example, a difference of 1.0 D or more), the analysis and control part 50 judges that the examination (measurement) was inappropriate and thus the monitor 7 displays a message to prompt the examiner that the distance refractive power measurement and the accommodative function examination must be executed again (S10).

In the above description, the astigmatic power and the astigmatic axis angle obtained in the previous distance refractive power measurement are utilized to correct the refractive power in the accommodative function examination. However, the astigmatic axis angle may vary with a change in the amount of accommodation applied to the eye. To avoid this defect, it is possible to adopt another manner of measuring refractive power in each meridian direction every time the presenting position of the fixation target is changed and, based on a result thereof, correcting the refractive power obtained at each presenting position in the accommodative function examination. In this case, refractive power in each meridian direction is first measured after movement of the fixation target to each presenting position. By using the switch part 8, the examiner can select on which astigmatism should be corrected; namely, based on the previous result of distance refractive power measurement or based on the result of refractive power measurement at each presenting position in the accommodative function examination.

Figure 6:
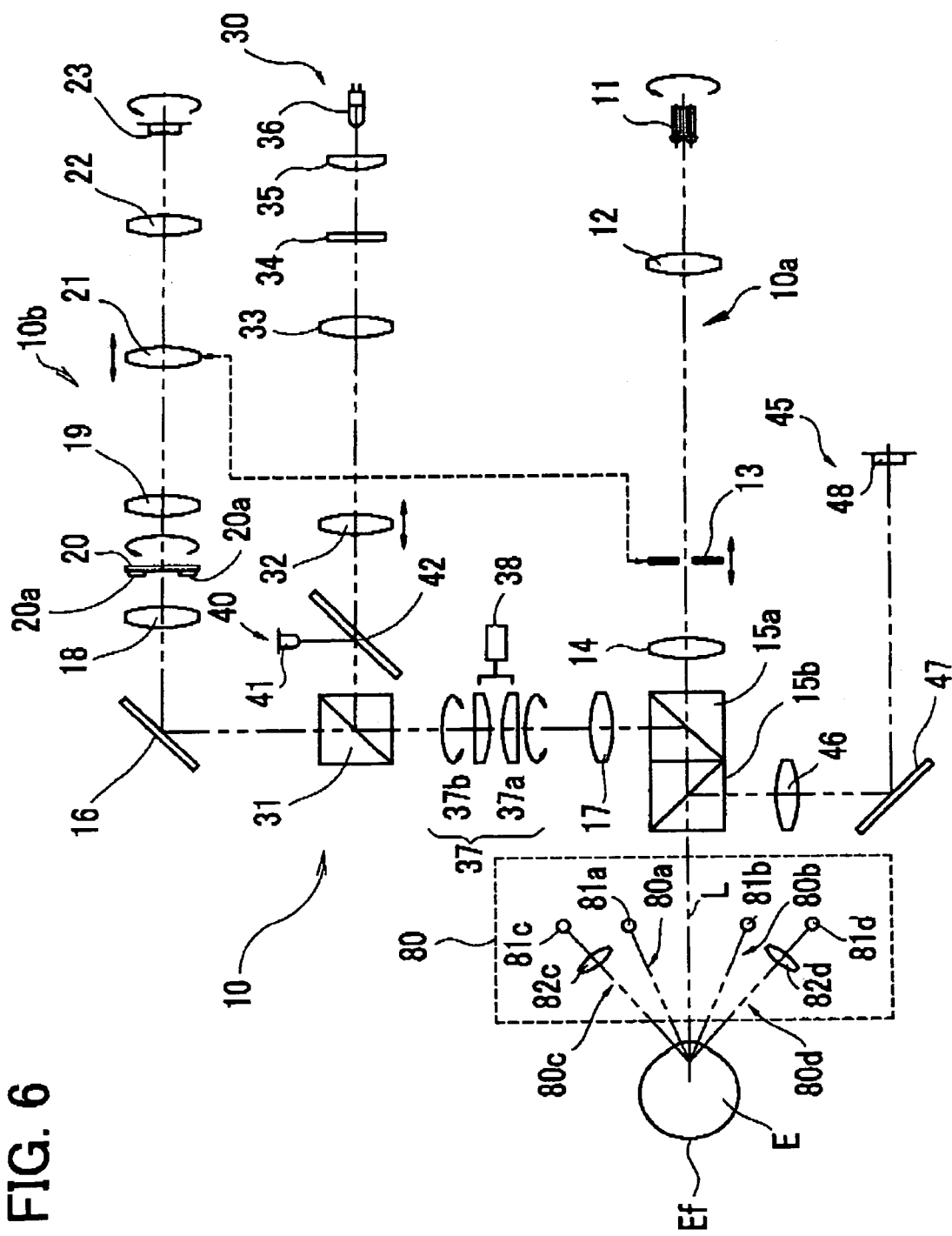
FIG. 6 is a schematic structural view of an optical system provided with an astigmatism correcting optical system.

FIG. 6 is a schematic structural view of the optical system provided with the astigmatism correcting optical system, with the same reference numerals for the same elements or components in FIG. 2. In FIG. 6, an astigmatism correcting optical system 37 is provided in an optical path (between the lens 17 and the half mirror 31) commonly used by the light receiving optical system 10*b* of the refractive power measurement optical system 10 and the fixation target presenting optical system 30. This astigmatism correcting optical system 37 includes two cylindrical plus lenses 37*a* and 37*b* which have an equal focal length and are independently rotatable about the optical axis L in the same or inverse direction. The lenses 37*a* and 37*b* are rotated by a drive part (a motor or the like) 38 which is controlled by the analysis and control part 50.

In the distance refractive power measurement with the above structure, the astigmatism correction by the astigmatism correcting optical system 37 is not conducted, but the regular refractive power measurement is executed as mentioned above to obtain each value S, C, and A, i e., to detect astigmatism. In the accommodative function examination, the analysis and control part 50 causes the drive part 38 to rotate the lenses 37a and 37b, thereby generating cylindrical power for correcting the value C of the measurement result while changing the axis angle according to the value A. In this way, the optical system for correcting the astigmatic state of the eye E is formed. Accordingly, refractive power corrected according to astigmatism regardless of the measurement meridian direction is obtained in the accommodative function examination. During presenting of the fixation target by the fixation target presenting optical system 30, further, the astigmatic state of the eye E is also corrected by the astigmatism correcting optical system 37. The eye E can stably look at the fixation target irrespective of the own astigmatic axis angle. It is to be noted that when two cylindrical lenses are used to generate an astigmatic (cylindrical) component, a spherical component which will occur in association with the generation of the astigmatic component has to be corrected.

As with the aforementioned example, the correction using the astigmatism correcting optical system 37 may be made based on the result of the refractive power measurement at each presenting position in the accommodative function examination. This manner makes it possible to particularly bring the eye in an exactly corrected state in the case where the astigmatic axis angle is likely to vary according to a change in the amount of accommodation to be applied to the eye.

The placement of the astigmatism correcting optical system 37 in the common optical path of the light receiving optical system 10b and the fixation target optical system 30 is advantageous for simplifying the structure of the apparatus. As a matter of course, the astigmatism correcting optical system 37 may be disposed in respective exclusive optical paths of the light receiving optical system 10b and the fixation target optical system 30, or, may be disposed in the light projecting optical system 10a instead of the light receiving optical system 10b.

In another alternative, the astigmatism correcting optical system 37 may be disposed only in the fixation target optical system 30 so that the refractive power is corrected in combination with processing by software in the calculation after measurement, as in the aforementioned example.

The refractive power measurement optical system is not limited to the above mentioned and may be selected from diverse systems. Such systems include for example a system of making ring-shaped measurement light enter the eye through the peripheral portion of the pupil to project the light to the fundus and receiving the reflection light from the fundus through the center portion of the pupil to form a ring image on a two-dimensional light receiving element (photodetector); a system of making spot-shaped measurement light enter the eye through the center portion of the pupil to project the light to the fundus and receiving the reflection light from the fundus through the peripheral portion of the pupil to form a ring image on a two-dimensional light receiving element (photodetector); and others. In any system, the values S, C, and A can be determined by analysis of the size and shape of the ring image. However, it should take long time to determine the ring shape by analysis of the ring image in all directions and therefore it is hard to acquire variation in refractive power within 0.1 second. In these cases, two coordinates in only a specified meridian direction, e.g., the horizontal meridian direction with reference to the center of the ring image, are partially detected and the refractive power in that direction is obtained based on the interval between the two coordinates. Thus, variation in the refractive power can be obtained at high speed. An error (deviation) by astigmatism in the measurement meridian direction can be corrected by the aforementioned astigmatism correcting process by calculation or the provision of the astigmatism correcting optical system.

Further, the fixation target presenting optical system is not limited to the above mentioned and may be selected from various systems.

Figure 4:
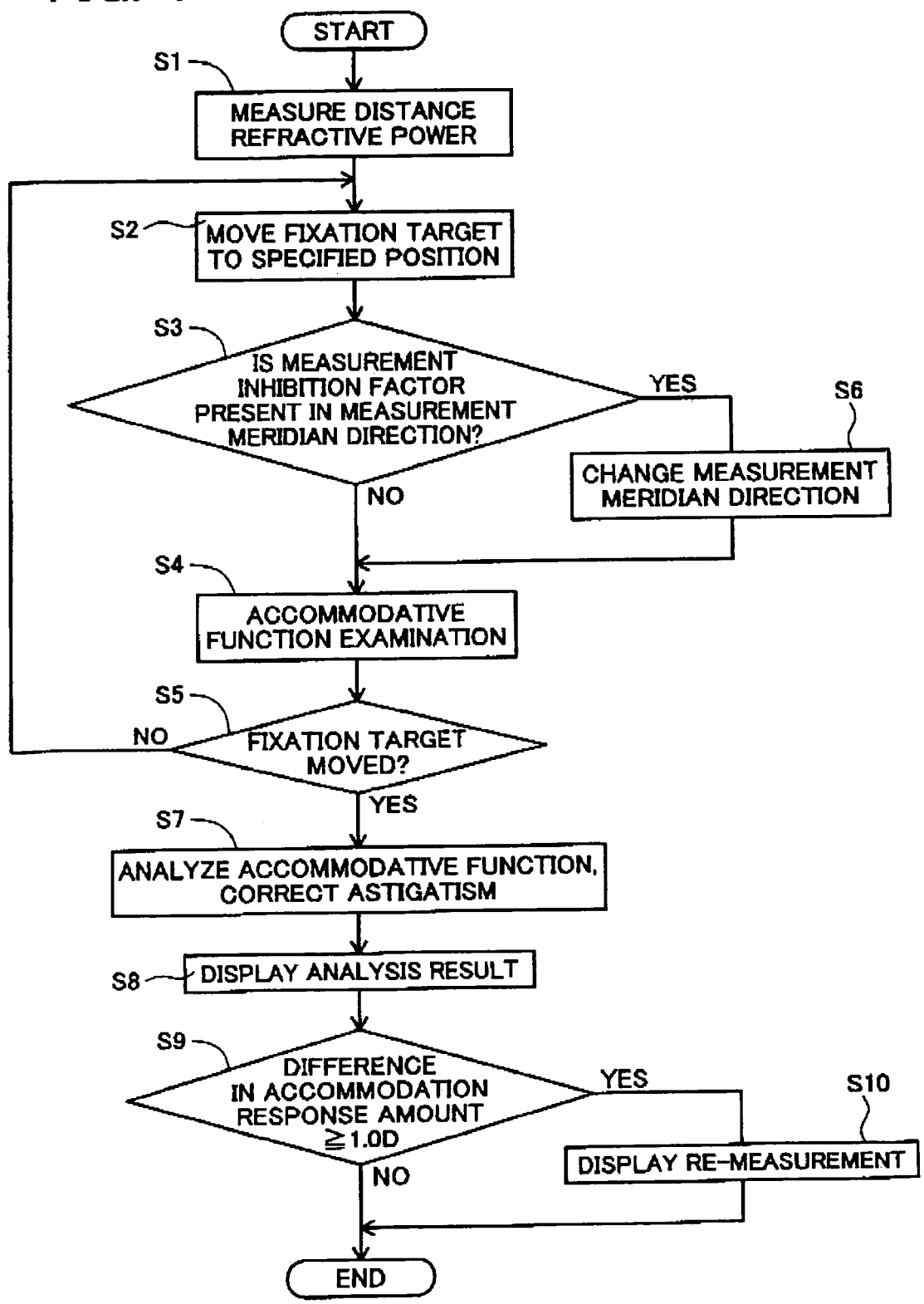
FIG. 4 is a flowchart to explain examination of an accommodative function.

The steps S7 and S8 in the flowchart in FIG. 4 may be conducted between the steps S4 and S5. Specifically, the analysis of the accommodative function, the astigmatism correction, and the display of the analysis result may be performed with respect to each fixation target presenting position.

While the presently preferred embodiment of the present invention has been shown and described, it is to be understood that this disclosure is for the purpose of illustration and that various changes and modifications may be made without departing from the scope of the invention as set forth in the appended claims.

What is claimed is:

1. An ocular accommodative function examination apparatus for examining an accommodative function of an examinee's eye, comprising:

a fixation target presenting optical system which presents a fixation target to the eye by changing an optical distance;

a refractive power measuring optical system which measures refractive power of the eye and includes a light projecting optical system which includes a light source and projects examination light to a fundus of the eye and a light receiving optical system which includes a light receiving element and receives the examination light reflected from the fundus;

a control part which operates the refractive power measuring optical system to measure distance refractive power of the eye including spherical power, cylindrical power, and an astigmatic axis angle while causing the fixation target presenting optical system to apply a fogging to the eye, and determines a first presenting position of the fixation target based on the distance refractive power and causes the presenting position of the fixation target to be optically changed sequentially in predetermined steps from the first presenting position toward the eye to measure variations with time of refractive power in a specified measurement meridian direction of the eye within a predetermined time at each presenting position of the fixation target; and an analysis part which corrects the variations with time of the refractive power in the specified measurement meridian direction at each presenting position of the fixation target to variations with time of refractive power in a minor meridian direction based on the cylindrical power and the astigmatic axis angle of the distance refractive power and then performs a frequency analysis of the variations with time of the refractive power in the minor meridian direction to calculate spectral power of a high frequency component of an accommodative microfluctuation of the eye at each presenting position of the fixation target.

2. The ocular accommodative function examination apparatus according to claim 1, wherein the analysis part corrects the variations with time of the refractive power in the specified measurement meridian direction at each presenting position of the fixation target to the variations with time of the refractive power in the minor meridian direction by using a predetermined calculation equation based on the cylindrical power and the astigmatic axis angle of the distance refractive power.

3. The ocular accommodative function examination apparatus according to claim 1, further comprising:
   a detecting device which detects a presence or absence of an inhibition factor to the refractive power measurement in the specified measurement meridian direction; and
   a changing device which changes the measurement meridian direction when the measurement inhibition factor is detected by the detecting device.

4. The ocular accommodative function examination apparatus according to claim 1, wherein the analysis part calculates a difference between converted refractive power from the presenting position of the fixation target and the refractive power in the specified measurement meridian direction and determines whether the difference is a predetermined value or more.

5. An ocular accommodative function examination apparatus for examining an accommodative function of an examinee's eye, comprising:
   a fixation target presenting optical system which presents a fixation target to the eye by changing an optical distance;
   a refractive power measuring optical system which measures refractive power of the eye and includes a light projecting optical system which includes a light source and projects examination light to a fundus of the eye and a light receiving optical system which includes a light receiving element and receives the examination light reflected from the fundus;
   an astigmatism correcting optical system provided in an optical path commonly used between the fixation target presenting optical system and the light receiving optical system;
   a control part which operates the refractive power measuring optical system to measure distance refractive power of the eye including spherical power, cylindrical power, and an astigmatic axis angle while causing the fixation target presenting optical system to apply a fogging to the eye, and causes the astigmatism correcting optical system to correct astigmatism and determines a first presenting position of the fixation target based on the distance refractive power, and causes the presenting position of the fixation target to be optically changed sequentially in predetermined steps from the first presenting position toward the eye to measure variations with time of refractive power in a specified measurement meridian direction of the eye within a predetermined time at each presenting position of the fixation target; and
   an analysis part which performs a frequency analysis of the variations with time of the refractive power to calculate spectral power of a high frequency component of an accommodative microfluctuation of the eye at each presenting position of the fixation target.

* * * * *